United States Patent [19]

Takagi et al.

[11] 4,347,204
[45] Aug. 31, 1982

[54] FLEXIBLE TUBE AND METHOD OF MANUFACTURING SAME

[75] Inventors: Takeji Takagi, Machida; Kiyokazu Hosaka, Fuchu, both of Japan

[73] Assignee: Olympus Optical Co., Ltd., Japan

[21] Appl. No.: 169,596

[22] Filed: Jul. 17, 1980

Related U.S. Application Data

[62] Division of Ser. No. 73,712, Sep. 10, 1979, Pat. No. 4,279,245.

[51] Int. Cl.$^3$ ............................................. A61B 1/00
[52] U.S. Cl. ........................................ 264/127; 427/2; 427/296; 264/129
[58] Field of Search ................ 128/4; 427/2, 296; 264/127, 129

[56] References Cited

U.S. PATENT DOCUMENTS

| | | | |
|---|---|---|---|
| 3,960,143 | 6/1976 | Terada | 128/4 |
| 4,082,893 | 4/1978 | Okita | 128/DIG. 14 |
| 4,208,745 | 6/1980 | Okita | 128/DIG. 14 |
| 4,279,245 | 7/1981 | Takagi | 128/4 |

FOREIGN PATENT DOCUMENTS 2903049  8/1979  Fed. Rep. of Germany .......... 128/4

*Primary Examiner*—Sam Silverberg
*Attorney, Agent, or Firm*—Ostrolenk, Faber, Gerb & Soffen

[57] ABSTRACT

A flexible tube and a method of manufacturing same and provided. The flexible tube comprises a tubular body of a crystalline polymer material having a porous microstructure including a number of micro-nodes which are coupled together by fibrils. A synthetic resin material having gas tightness and stretchability is filled into the pores of the porous microstructure.

8 Claims, 4 Drawing Figures

FIG. 1
FIG. 2
FIG. 3
FIG. 4
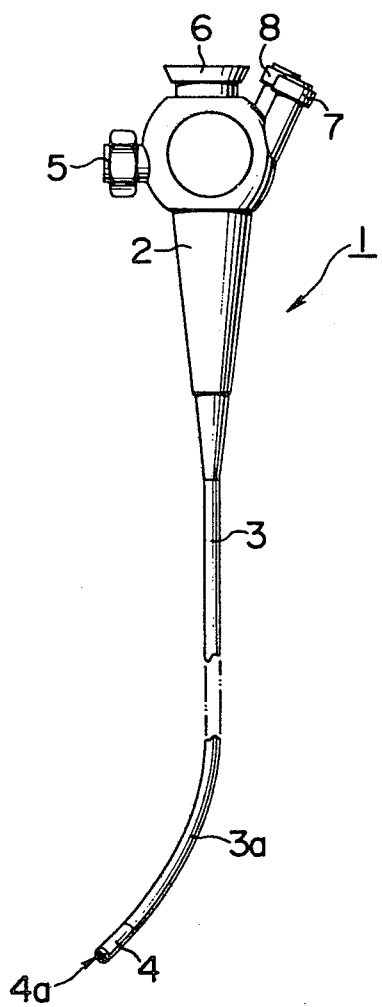
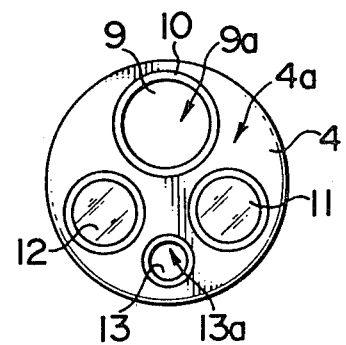
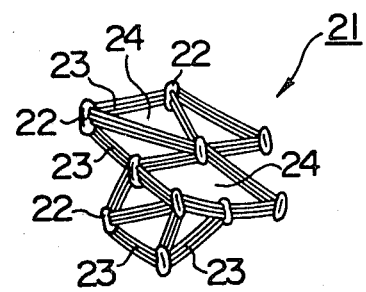
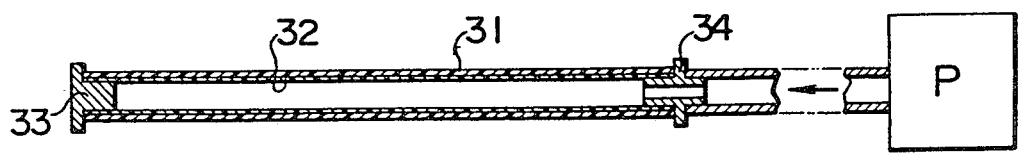

FLEXIBLE TUBE AND METHOD OF MANUFACTURING SAME

This is a division of application Ser. No. 73,712, filed Sept. 10, 1979 and now U.S. Pat. No. 4,279,245.

BACKGROUND OF THE INVENTION

The invention relates to a flexible tube and a method of manufacturing some, and more particularly, to a flexible tube having a reduced radius of curvature, a high bending capability and a gas tightness which may be used in forming a forceps channel, or a gas or water feed channel of an endoscope used for medical purposes, and a method of manufacturing same.

A medical endoscope which is used to provide an observation of coeloma of a living body or a treatment of an affected part therein is constructed in a manner as illustrated in FIG. 1, which shows an endoscope of a direct view type. Specifically, endoscope 1 includes an operating end 2 which is connected with a flexible tube which defines portion 3 of the endoscope which is adapted to be inserted into coeloma. The operating end 2 is located outside a physical body and is subject to a variety of manual operations. The operating end 2 is provided with a number of accessories including bend operator 5 which is used to bend the free end of the endoscope portion 3 in a desired direction, an observation eyepiece assembly 6, forceps receiver 7 which is utilized to insert forceps into forceps channel 9 formed by flexible tube 10 (see FIG. 2), and fittings 8 which are used to feed a gas or water into gas/water feed channel 13 (see FIG. 2) also formed by a flexible tube.

The free end of the endoscope portion 3 is fixedly provided with end fixture 4 which includes a channel opening, an illumination and an observation window. Referring to FIG. 2, end fixture 4 has front end face 4a in which illumination window 11 and observation window 12 are located symmetrically with respect to the center line thereof for enabling an illumination and an observation of a desired area within coeloma. Also formed in the end face 4a are opening 9a associated with forceps channel 9 and opening 13a associated with gas/water feed channel 13 above and below these windows, respectively.

An objective lens, not shown, is disposed inside observation window 12 in opposing relationship therewith, and constitutes an observation optical system together with an eyepiece, not shown, located within the eyepiece assembly 6 and a flexible image guide formed by a bundle of optical fibres which extend between the both lenses to conduct light therebetween.

One end face of a light guide, not shown, which is constructed in a conventional manner, is located inside illumination window 11 in opposing relationship therewith while the other end face of the light guide is located within the operating end 2 in opposing relationship with an illumination light emitting port of a light source disposed therein, whereby light from the source is directed through the light guide and illumination window 11 to irradiate a desired area within coeloma which is to be observed.

The flexible tube which forms the endoscope portion 3 to be inserted into coeloma has a very small radius of curvature in its region 3a which is subject to an increased degree of bending, and in a corresponding manner, flexible tubes such as tube 10 which defines forceps channel 9 also have a reduced radius of curvature. In addition to high degree of bending capability, gas and water tightness is required of these flexible tubes such as tube 10 in order to prevent an ingress of coeliac fluid into the flexible tubes because their front ends are open into the coeloma. Furthermore, they should be free from kinks, crushing, wrinkles in the tube walls and should have a smooth internal wall surface.

However, there is known no conventional tubes of this kind which are free from kinks, crushing or surface wrinkles when they are bent into a diameter which is as small as ten times the diameter (R) of the tubes themselves. If the tubes are free from kinks or crushing when bent to a diameter of 10R, a greater force is required during their manufacturing or a special treatment such as the application of heat or pressure is required in order to bend these tubes into such diameters. Although a multi-layer tube is known in the prior art, the purpose of the lamination is to improve the pressure resistance of the tube, and is not directed to an improvement of the bending capability, flexibility, or the freedom from kinks when bent into small radii. In short, there is no flexible tube having a gas and water tightness and which is adapted to be used in the manner mentioned above, and therefore it will be appreciated that there has been a strong need for the provision of such flexible tube.

SUMMARY OF THE INVENTION

It is an object of the invention to provide a flexible tube which satisfy the described requirements, by providing a tubular body formed of a crystalline polymer material having porous microstructures including a number of micro-nodes which are coupled together by fibrils and in which the pores in the microstructures are filled with a gas tight and stretchable plastic material, and a method of manufacturing same.

In accordance with the invention, there is provided a flexible tube which has improved performances over conventional flexible tube, and which can be manufactured in a simple and inexpensive manner.

BRIEF DESCRIPTION OF THE DRAWINGS

FIG. 1 is a front view of an endoscope of a direct view type incorporating flexible tubes to define forceps channel and gas/water feed channel;

FIG. 2 is an enlarged end view of a front end face of a portion of the endoscope shown in FIG. 1 which is adapted to be inserted into coeloma;

FIG. 3 is an enlarged illustration of porous microstructures of a crystalline polymer material; and FIG. 4 is a cross section illustrating one step of a method of manufacturing a flexible tube in accordance with the invention.

DESCRIPTION OF PREFERRED EMBODIMENT

A flexible tube which is manufactured in accordance with the invention utilizes a tubular body formed of a crystalline polymer material having porous microstructures which include a number of micro-nodes coupled together by fibrils. Preferred crystalline polymer materials include fluorine resins and polyolefins. Specific examples of fluorine resins include polytetrafluoroethylene (PTFE) to which may or may not be added an extractable inorganic additive such as silicate, carbonate, metal, metal oxide, sodium chloride, ammonium chloride or the like, or an organic powder such as a powder of a copolymer of tetrafluoroethylene and hexafluoropropylene (FEP), starch, sugar or the like. A specific example of polyolefins includes a polypropylene resin.

FIG. 3 is an enlarged perspective view showing part of porous microstructures of PTFE where a number of micro-nodes 22 are connected together by fibrils 23, leaving a number of spaces 24 therebetween.

A method will now be described of manufacturing a tube from a crystalline polymer material having such porous microstructures of PTFE. Initially, a liquid lubricant such as hydrocarbon oil, for example, solvent naphtha, white oil or petroleum ether is added to and mixed with a fine powder of PTFE or a coagulate of PTFE at a mixture ratio of 80:20 for PTFE and liquid lubricant. A small quantity of organic or inorganic additive may then be added with the mixture to form a compact, which is then extruded through a ram extruder into a tubular form, thus producing a molded product.

The liquid lubricant is then removed from the molded product. Though the liquid lubricant may be left in the product, the resulting final product is poor in quality. While it is unsintered (kept below 327° C.), it is lengthwise stretched to 1.2 to 15 times its original length. The internal strains in the stretched product are then thermally fixed at a temperature higher than its melting point or slightly less than that, preferably at a temperature between 200° and 390° C.

The crystalline polymer material having porous microstructures of PTFE thus obtained has an enhanced pliability, flexibility, heat resistance, chemical resistance, water repellency, non-adherence, sliding characteristic, stretchability, and elastic recovery. Usually, it has a wall thickness of 0.05 to 3.5 mm, in particular, 0.1 to 2.0 mm, a porosity of 30 to 90%, in particular, 60 to 80%, an average diameter of pores from 0.01 to 20 microns, in particular, 1 to 5 microns, a Gurley number (the length of time required for 100 c.c. of air to permeate under a pressure of 12.7 mm Hg through a cross-sectional area of 6.45 $cm^2$ of 0.01 to 5000 seconds and, a water leakage pressure of 0.1 to 1.5 $kg/cm^2$. These properties can be varied as desired over a wide range by controlling the manufacturing parameters, thus enabling an intended material to be easily obtained.

A gas tightness and a water tightness are imparted to the resulting flexible tube in a manner mentioned below. A flexible tube is formed to have desired internal and external diameters and a desired length, and a solution of a plastic material having a gas/water tightness is uniformly applied to the internal surface of the tube to a thickness which is substantially comparable to the wall thickness of the tube. Such plastic materials may comprise FEP, fluorine resins such as a copolymer of ethylene tetrafluoride and perfluoroalkyl vinyl ether, fluorine rubber, polyurethane, polyimide, polyester, nylon, polyvinyl chloride, polyethylene or the like.

FIG. 4 shows tube 31 having plastic material 32 applied to its internal surface. One end of the tube is closed by plug 33 while connecting pipe 34 is hermetically fitted into the other end of the tube for pumping air into tube 31 by utilizing pump P. When the air is pumped into tube 31, the plastic material 32 permeates into pores 24 (see FIG. 3) of tube 31 under the air pressure, thus filling these pores. At the completion of the filling operation, pump P is deactuated, and plastic material 32 which is filled into tube 31 is allowed to solidify, whereupon connecting pipe 34 is disconnected from tube 31 and plug 33 also removed therefrom.

The resulting flexible tube 31 may be used as tube 10 which defines the forceps channel (see FIG. 2). The tube 10 has all of the required characteristics including the gas/water tightness and high flexibility, and is also free from kinks, crushing and wrinkles in the tube wall. Additionally, the tube has a smooth internal wall surface.

It should be understood that a tube which defines the air/water feed channel can be manufactured in the same way.

While in the arrangement of FIG. 4, the pressure has been applied to the internal surface of tube 31 in order to fill plastic material 32 into the pores of tube 31, it should be understood that a suction may be applied to the external surface of the tube. Alternatively, after applying plastic material 32 to the external surface of tube 31, a pressure may be applied to the external surface simultaneously with a suction applied to the internal surface of tube 31.

While in the foregoing description, flexible tube 10 has been described as one used to form a forceps channel of an endoscope, it should be understood that the tube can equally be used in a small size fluid controlling instrument, piping between instruments or a variety of conduits of industrial endoscopes for which the described requirements of the tube are essential.

What is claimed is:

1. In a method of manufacturing an endoscope comprising forming a flexible tube wherein the steps comprise forming a tubular body of a crystalline polymer material having a porous microstructure including a number of micro-nodes which are coupled together by fibrils, applying a solution of synthetic resin material having gas tightness and stretchability to one of the internal and external peripheral surfaces of the tubular body, and subsequently applying a pressure or suction to either peripheral surface of the tubular body to cause the solution of the synthetic resin material to permeate into the pores of the porous microstructure of the tubular body, thus filling the pores.

2. A method of manufacturing a flexible tube according to claim 1 in which the crystalline polymer material comprises a fluorine resin or polyolefin.

3. A method of manufacturing a flexible tube according to claim 2 in which the fluorine resin comprises polytetrafluoroethylene.

4. A method of manufacturing a flexible tube according to claim 2 in which the polyolefin comprises a polypropylene resin.

5. A method of manufacturing a flexible tube according to claim 1 in which the synthetic resin material comprises a fluorine resin, polyurethane, polyimide, polyester, nylon, polyvinyl chloride or polyethylene.

6. A method of manufacturing a flexible tube according to claim 1 in which the tubular body is formed by the steps of adding to a fine powder of polytetrafluoroethylene or a coagulate thereof a liquid lubricant at a ratio of 80:20 for polytetrafluoroethylene and liquid lubricant, mixing both together, forming a compact with the mixture, utilizing a ram extruder to extrude the compact into a tubular form, thereby forming a molded product, stretching the molded product lengthwise to 1.2 to 15 times its original length while in its unsintered condition (below 327° C.), and thermally fixing the internal strains in the stretched product in its stretched condition at a temperature above or slightly below its melting point.

7. A method of manufacturing a flexible tube according to claim 2 in which the fluorine resin comprises polytetrafluoroethylene containing extractable silicate, carbonate, metal metal oxide, sodium chloride, ammonium chloride, copolymer of tetrafluoroethylene and hexafluoropropylene, starch or sugar.

8. The method of claim 6, wherein the thermal fixing is at a temperature between 200° and 390° C.

* * * * *